United States Patent
Choi et al.

(10) Patent No.: US 9,295,655 B2
(45) Date of Patent: Mar. 29, 2016

(54) FENTANYL TRANSDERMAL PATCH

(75) Inventors: Young Kwen Choi, Seoul (KR); Jung Ju Kim, Seoul (KR); Jung Sik Lee, Suwon-si (KR); Sung Soo Kim, Seongnam-si (KR)

(73) Assignee: Icure, Seoul (KR)

( * ) Notice: Subject to any disclaimer, the term of this patent is extended or adjusted under 35 U.S.C. 154(b) by 161 days.

(21) Appl. No.: 14/004,889

(22) PCT Filed: Mar. 13, 2012

(86) PCT No.: PCT/KR2012/001809
§ 371 (c)(1),
(2), (4) Date: Sep. 12, 2013

(87) PCT Pub. No.: WO2012/124966
PCT Pub. Date: Sep. 20, 2012

(65) Prior Publication Data
US 2014/0005617 A1    Jan. 2, 2014

(30) Foreign Application Priority Data
Mar. 15, 2011    (KR) .................. 10-2011-0022958

(51) Int. Cl.
| | |
|---|---|
| A61K 9/70 | (2006.01) |
| A61K 31/4468 | (2006.01) |
| A61M 35/00 | (2006.01) |
| A61F 13/02 | (2006.01) |
| A61L 15/44 | (2006.01) |
| A61L 15/58 | (2006.01) |
| A61K 31/454 | (2006.01) |

(52) U.S. Cl.
CPC ............. *A61K 9/7076* (2013.01); *A61F 13/02* (2013.01); *A61F 13/0246* (2013.01); *A61K 9/7053* (2013.01); *A61K 31/4468* (2013.01); *A61K 31/454* (2013.01); *A61L 15/44* (2013.01); *A61L 15/58* (2013.01); *A61M 35/00* (2013.01); *A61L 2300/402* (2013.01)

(58) Field of Classification Search
None
See application file for complete search history.

(56) References Cited

U.S. PATENT DOCUMENTS

| 5,688,524 | A | * | 11/1997 | Hsu et al. | ........ 424/449 |
|---|---|---|---|---|---|
| 6,139,866 | A | | 10/2000 | Chono et al. | |
| 7,504,114 | B1 | | 3/2009 | Kurita et al. | |
| 2007/0179373 | A1 | * | 8/2007 | Pronovost | ........ 600/362 |

(Continued)

FOREIGN PATENT DOCUMENTS

| KR | 10-1998-0025307 | 7/1998 |
|---|---|---|
| KR | 10-0563194 B1 | 3/2006 |

(Continued)

OTHER PUBLICATIONS

PCT International Search Report for PCT Counterpart Application No. PCT/KR2012/001809, 7 pgs., (Sep. 25, 2012).

(Continued)

*Primary Examiner* — Ernst V Arnold
*Assistant Examiner* — Jianfeng Song
(74) *Attorney, Agent, or Firm* — Blakely, Sokoloff, Taylor & Zafman LLP

(57) ABSTRACT

Provided is a fentanyl transdermal patch comprising an acrylic-rubber hybrid as a drug-adhesive layer. The fentanyl transdermal patch can maintain constant fentanyl skin permeability for three days by maintaining close contact with the skin such that desorption, release by moisture and sweat, and skin stimulation are all improved.

11 Claims, 2 Drawing Sheets

(56) References Cited

U.S. PATENT DOCUMENTS

2009/0004257 A1* 1/2009 Venkatraman et al. ....... 424/449
2009/0098191 A1* 4/2009 Anderson et al. ............. 424/443
2009/0246263 A1 10/2009 Honma et al.

FOREIGN PATENT DOCUMENTS

KR 10-0844312 B1 7/2008
WO WO 02/074286 A1 9/2002

OTHER PUBLICATIONS

Stefan Grond, et al., "Clinical Pharmacokinetics of Transdermal Opioids: Focus on Transdermal Fentanyl", Clin. Pharmacokinet., vol. 38, No. 1, pp. 59-89, (Jan. 2000).
PCT Notification of Transmittal of International Preliminary Examination Report for PCT Application No. PCT/KR2012/001809, 8 pgs. (Sep. 26, 2013).

* cited by examiner

FENTANYL TRANSDERMAL PATCH

CROSS-REFERENCE TO RELATED APPLICATIONS

This patent application is a U.S. National Phase Application under 35 U.S.C. § 371 of International Application No. PCT/KR2012/001809, filed Mar. 13, 2012, entitled FENTANYL TRANSDERMAL PATCH, which claims priority to Korean Patent Application No. 10-2011-0022958, filed Mar. 15, 2011.

FIELD

The present invention relates to a fentanyl transdermal patch. More particularly, the present invention relates to a fentanyl transdermal patch that includes a drug-adhesive layer comprising an acrylic-rubber hybrid to prevent detachment due to excessive moisture and sweat, thereby maintaining constant fentanyl skin permeability while maintaining close contact with the skin.

BACKGROUND

In the present invention, terms such as transdermal patch, transdermal absorption patch, transdermal administration patch etc. represent solid preparations (solidified preparations) of transdermal drug delivery systems for delivering drugs through the skin.

Pain is recognized by nociceptors and other neural cells associated with pain inducing pathways by responding to stimuli and sending signals via the spinal cord to the brain. Fentanyl and its derivatives are opioids and exhibit analgesic activity by binding to opiate receptors of spinal cord and inhibiting release of neurotransmitters, thereby preventing pain signals from being delivered to spinal cord neurons. Opioids may be effectively used for all kinds of pain relief from moderate to severe pain due to their efficacy and advantages such as convenient titration and risk-to-benefit ratio, contrary to NSAIDs having a ceiling effect in analgesic activity.

Fentanyl is suited to transdermal administration. When fentanyl is administered transdermally, fentanyl may be administered by simple attachment, and may have merits in that fentanyl is not passed through liver first-pass metabolism, and has improved patient convenience and medication compliance, constant analgesic activity, lessened nursing effort, reduced sleep interference etc. Fentanyl preparations administered transdermally may be used particularly in cancer patients. When body temperature is increased due to cancer, reaction time of fentanyl may be shortened due to increased absorption amount from subcutaneous tissues.

Examples of fentanyl transdermal preparations that are already commercially available include Durogesic (Janssen), Durogesic D-trans patch (Janssen), Fentanyl Transdermal System CII (Mylan, Teva, Watson), Fenstud (Rusan) etc. These preparations, aside from Durogesic and Durogesic D-trans patches, are all generic medicines. Durogesic is a reservoir type and is designed such that fentanyl is mixed and dissolved in a liquid drug-containing layer consisting of ethanol and water. This reservoir type transdermal administration preparation comprises a backing layer, a reservoir layer of gel containing a drug and ethanol as a transdermal absorption enhancer, a membrane layer to control release rate, an adhesive layer and a detachable layer. Accordingly, the reservoir type transdermal preparation has merits that the release rate of drugs is easily controlled and skin permeation is accelerated. However, owing to irritation caused by ethanol used as a skin permeation accelerator, one may suffer side effects such as skin irritation or the like when the preparation is used for long time, for example, for three days or so. In addition, the preparation has disadvantages in that production of the preparation requires considerably complicated production processes since the preparation comprises several layers, the preparation has a bad sense of skin attachment and efficacy of the preparation is exhibited only after 12 hours or more (lag time). Further, if the reservoir of the reservoir type fentanyl transdermal preparation leaks, there are disadvantages in that the content in the active compound-containing reservoir comes into contact with the skin over wide area, and thus the active compound is absorbed in an excessive dose amount. Especially, when fentanyl and its derivatives are administered to a human in an excessive amount, it is particularly dangerous since rapid respiratory decline may occur, possibly resulting in death (Clinical Pharmacokinetics. 2000, 38(1), 59-89).

In order to overcome such disadvantages, matrix type monolithic patches have been developed using acrylic adhesives. These preparations have achieved some improvement in their performance such as stable delivery of drugs, reduction in skin irritation by ethanol etc. However, these preparations still have problems in that detachment by moisture and sweat, and skin irritation due to adhesiveness of the monolithic patches are not completely solved.

Further, in an attempt to shorten lag time, patches to induce rapid release of drugs have been developed using silicone type or rubber type adhesives having a fast spread rate and low fentanyl solubility. As silicone type adhesives, matrix type fentanyl patches using amine-resistant polydimethyl siloxane have been developed. As rubber type adhesives, an adhesive-base has been prepared by mixing high molecular weight and low molecular weight polyisobutylenes (PIB), or matrix type fentanyl patches including styrene block copolymer styrene-isoprene-styrene (SIS) and polyisobutylene (PIB) have been designed. These patches have the effects that the skin permeation rate of drugs is increased, thereby decreasing patch area. Since high molecular weight polyisobutylenes constituting the matrix of preparations are excessively hydrophobic, the patches still have problems of detachment due to sweat or moisture.

When a preparation is prepared by including a matrix layer formed by two adjacent adhesive polymers layers having different fentanyl solubilities, a certain amount of fentanyl is rapidly released from the adhesive polymer layer having a low fentanyl solubility at an early stage of administration to shorten time for reaching an effective blood concentration, thereby moving up the onset time of analgesic effects. When a predetermined time has passed, a drug may be released from the adhesive polymer layer having a high fentanyl solubility sufficient to maintain the effective blood concentration, thereby maintaining long-term analgesic effects. However, in order to produce the preparation, two kinds of drug-containing adhesive solutions should be separately prepared. Namely, one drug-containing adhesive solution is applied to a backing layer, while the other drug-containing adhesive solution is applied to a detachable layer, followed by drying. The two drug-containing adhesive layers should be accurately placed facing each other without overlapping. Subsequently, in order to prepare the preparation, the opposite drug-containing adhesive layers should be accurately cut so that the preparation has a certain area of the two drug-containing adhesive layers. In this context, the process for producing the preparation is complicated. Additionally, the loss rate of fentanyl occurring during the process is very high.

Therefore, there is a need for a new fentanyl transdermal patch which can be prepared simply, deliver fentanyl constantly for long time (three days), maintain long term skin attachment and does not have side effects of skin irritation.

SUMMARY

After intensive studying to produce a transdermal absorption patch capable of delivering fentanyl consistently for long durations and maintaining skin attachment for long durations, it was found that that the use of an acrylic-rubber hybrid as a drug-adhesive layer leads to a patch of the present invention, which can be prepared in a simple manner, deliver fentanyl constantly for long durations through the skin, and has improved attachment.

Accordingly, it is an object of the present invention to provide a fentanyl transdermal patch containing an acrylic-rubber hybrid as a drug-adhesive layer to prevent detachment from the skin due to moisture or sweat, thereby providing consistent transdermal delivery of fentanyl for three days while maintaining close contact with the skin.

In order to accomplish the above and other objects, embodiments of the invention provide fentanyl transdermal patches including a backing layer and a drug-adhesive layer at one side of the backing layer, wherein the drug-adhesive layer includes an acrylic-rubber hybrid polymer and, as a drug, fentanyl, fentanyl derivatives or pharmaceutically acceptable salts thereof.

If necessary, the fentanyl transdermal patch according to the present invention may further include a peripheral adhesive film and/or a detachable film layer at one side of the patch.

In the present invention, the drug-adhesive layer includes an acrylic-rubber hybrid polymer and a drug.

The acrylic polymer may or may not have a functional group depending on monomers to be used, and have good drug solubility and high resistance to moisture. However, owing to generally high drug solubility, the acrylic polymer has inferior dermal absorption of drugs as compared to that of rubber type and silicone type polymers. For this reason, in the case of using the acrylic polymer as an adhesive base, drugs may be contained in high concentration or a transdermal absorption enhancer may be used. On the other hand, the rubber type and silicone type polymers have high skin permeation and spread of drugs. However, there are problems in that the rubber and silicone materials themselves have high hydrophobicity, which weakens adhesion due to moisture and sweat.

The acrylic-rubber hybrid polymer may be a polymer formed by grafting a low molecular weight rubber macromer to an acrylic backbone.

In general, as a monomer to form the acrylic backbone, monomers having a low glass transition temperature (impart initial adhesion) such as 2-ethylhexyl acrylate, butyl acrylate, or isooctyl acrylate, monomers having a high glass transition temperature (impart adhesion) such as methyl acrylate or methyl methacrylate, and monomers having a functional group (impart functional group and adhesion) such as acrylic acid or 2-hydroxyethyl acrylate etc. are used. Additionally, monomers such as vinyl acetate may be used. Examples of the rubber macromer may include polyethylene-butylene or the like having for example methacrylate as an end group. When a rubber macromer is grafted to the acrylic backbone, the acrylic-rubber hybrid polymer may additionally have hydrophobic domains.

The acrylic-rubber hybrid polymer may be prepared by solution, dispersion or emulsion polymerization through radical reaction. For example, the radical polymerization may be performed using an acrylic type (alkyl ester type) monomer as a main monomer, a rubber macromer having a double bond at an end group as a comonomer and a radical initiator such as AIBN (azobis(isobutylronitrile). Since such polymerization has higher reactivity with the acrylic monomer than with the rubber monomer, an acrylic-rubber hybrid polymer may be formed having the structure represented below and having a low molecular weight rubber type polymer in the acrylic backbone as side chains.

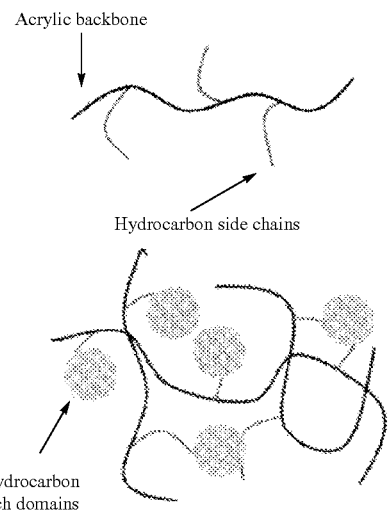

Because of this hydrophobic domain, the merit of hydrophobicity may be imparted to the acrylic polymer having a functional group, thereby increasing solubility of the hydrophobic drug or easily mixing a hydrophobic additive (for example, hydrocarbon resin tackifying resin or terpene tackifying resin, mineral oil, polybutene etc.) to the adhesive layer. Further, the high drug releasing property of the rubber may be provided to the acrylic backbone, thereby attaining the merits of the two polymers.

The acrylic-rubber hybrid polymer may be used by polymerizing as explained above, or commercially available Duro-Tak (Henkel Corporation) such as Duro-Tak 87-502A, Duro-Tak 87-503A, or Duro-Tak 87-504A or the like may be used. Acrylic-rubber hybrid polymers from other manufacturers may also be used.

In the present invention, the acrylic-rubber hybrid polymer may be present in an amount of 60 parts by weight to 95 parts by weight of the drug-adhesive layer. If the content of the acrylic-rubber hybrid polymer is 60 parts by weight or less, the adhesive properties or coherence of the polymer are severely damaged, and thus the patch fails to exhibit suitable physical properties. Further, if the content of the acrylic-rubber hybrid polymer is 95 parts by weight or more, drug concentration is too low to deliver the drug through the patch into the body in a required amount.

Examples of fentanyl as a drug used in the present invention may include fentanyl in free base form or derivatives thereof such as alfentanyl, carfentanyl, lofentanyl, remifentanyl, sufentanil and trefentanyl, or pharmaceutically available salts thereof. The pharmaceutical salts may be salts of inorganic acids such as hydrochloric acid, nitric acid, phosphoric acid, sulfuric acid, hydrobromic acid, hydroiodic acid, nitrous acid or phosphorous acid, or salts of innoxious organic acids such as aliphatic mono- and dicarboxylate, phenyl-substituted alkanoate, hydroxy alkanoate and alkanedioate, aromatic acids, aliphatic and aromatic sulfonic acid.

In the present invention, fentanyl is preferably present in an amount of 5 parts by weight to 20 parts by weight in the drug-adhesive layer. If the content of fentanyl in the drug-adhesive layer is less than 5 parts by weight, the drug concentration in the formulation is too low to deliver the drug to the body in a required amount. If the content of fentanyl is 20 parts by weight or more, although transdermal drug absorption is increased, the thickness of the preparation becomes excessively decreases, making it difficult to form the patch. Further, transdermal absorption of the drug is too high and exposes a patient to excessive drug concentrations, which poses a health hazard.

Specifically, if fentanyl is present in more than effective blood concentration, there may be side effects such as respiratory depression, muscular rigidity or the like. For these reasons, it is necessary to maintain a constant blood concentration, where the most important factors are a drug concentration in the drug-adhesive layer and solubility of the drug in the adhesive base (polymer). As the transdermal absorption degree and the drug concentration increase, the transdermal absorption degree becomes proportional to the drug concentration in patches having the same area and content. Under the same condition, the drug's solubility in the adhesive base is inversely proportional to the transdermal absorption degree. It is estimated that the acrylic-rubber hybrid polymer has drug solubility between the acrylic type adhesive and the rubber type adhesive.

In the present invention, various additives may be used in the drug-adhesive layer. Examples of such additives may include transdermal absorption enhancers, tackifiers, plasticizers, antioxidants, fillers etc.

The drug-adhesive layer of the present invention may contain a transdermal absorption enhancer in order to improve drug permeation rate to the skin. Examples of the transdermal absorption enhancer may include pyrrolidone derivatives, $C_{8-18}$ fatty acid derivatives, triacetin etc. As pyrrolidone derivatives, N-methyl-2-pyrrolidone, N-caprylyl-2-pyrrolidone, N-dodecyl-2-pyrrolidone etc. are preferred. N-dodecyl-2-pyrrolidone (Lauryl pyrrolidone) is more preferred. As $C_{8-18}$ aliphatic derivatives, glycerol lauryl alcohol, oleyl alcohol, isopropyl myristate, sorbitan monooleate, propylene monolaurate, propylene monooleate, oleyl macrogoglyceride, oleic acid, lauroyl macrogoglyceride, linoleoyl macrogoglyceride, propylene glycol caprylate/caprate, sorbitan monostearate monooleate, glycerol monolaurate, propylene glycol monolaurate, propylene glycol monocaprylate, sorbitan monolaurate, lauryl lactate, caprylic/capric triglyceride, corn oil PEG-8 ester, corn oil PEG-6 ester etc. are preferred. Glycerol monooleate, glycerol monolaurate, propylene glycol monolaurate, propylene glycol monocaprylate, sorbitan monolaurate etc. are more preferred.

In the present invention, the transdermal absorption enhancer may be used alone or in combination of two or more thereof. Further, the transdermal absorption enhancer is preferably present in an amount of 5 parts by weight to 20 parts by weight, more preferably 5 parts by weight to 15 parts by weight, based on the total amount of the drug-adhesive layer, thereby minimizing dermal side effects.

In the present invention, in order to improve adhesive properties, the drug-adhesive layer may contain a tackifier, which serves to enhance adhesion properties (initial adhesion, adhesion maintenance, coherence) of the base. Examples of the tackifier may include natural or petrochemical resin type, hydrophilic high molecular weight type, low molecular weight polybutene etc. As the natural or petrochemical resin type, there are rosin ester type resin, terpene type resin, aliphatic hydrocarbon resin, cycloaliphatic hydrocarbon resin, DCPD (dicyclo pentadiene), coumarone-indene etc. These resin types serve to enhance initial adhesion, adhesion maintenance, coherence etc., depending on the types of resins. As the hydrophilic high molecular weight type, there are pyrrolidone polymers such as polypyrrolidone, acrylic polymers such as polyacrylate, cellulose derivatives, such as hydroxypropyl cellulose etc. These hydrophilic polymers enhance coherence and maintain adhesion even when brought into contact with moisture released from the skin. Polybutene is a liquid phase polymer mainly comprised of isobutylene and having various low molecular weight forms due to low temperature and catalytic polymerization, and provides initial adhesion, adhesion maintenance, and plasticity to the adhesives. When the tackifier is a resin, the resin is preferably present in an amount of 1 part by weight to 10 parts by weight, more preferably 5 parts by weight to 10 parts by weight. When the tackifier is a hydrophilic polymer, the polymer is preferably present in an amount of 1 part by weight to 10 parts by weight, more preferably within 5 parts by weight. When the tackifier is polybutene, polybutene is preferably present in an amount of 5 parts by weight to 20 parts by weight, more preferably 5 parts by weight to 15 parts by weight.

In the present invention, in order to provide plasticity, the drug-adhesive layer may contain a plasticizer, which serves to increase flexibility of the adhesive base. Examples of the plasticizer may include mineral oil, polybutene, various C8~C18 higher fatty acids or esters or derivatives thereof etc. The plasticizer is preferably present in an amount of 1 part by weight to 10 parts by weight, more preferably 5 parts by weight to 10 parts by weight.

In the present invention, in order to prevent oxidation of drug and polymer, the drug-adhesive layer may contain an antioxidant. Examples of antioxidants may include tocopherols, propylgallic acid, butylhydroxy toluene (BHT), butyl hydroxyanisole (BHA) etc. The antioxidant is preferably used in an amount of not more than 1 part by weight.

In the present invention, in order to enhance mechanical strength, the drug-adhesive layer may contain fillers. Examples of fillers may include zinc oxide, titanium oxide, porous silica or the like. The fillers are preferably present in an amount of 1 part by weight to 20 parts by weight, more preferably 5 parts by weight to 15 parts by weight.

In the present invention, the backing layer prevents fentanyl from being oppositely spread and is only administered in a direction of the skin. The backing layer may be one selected from the group consisting of polyester films, aluminum-deposited polyester films, multi-deposited films, or non-woven fabric-laminated polyester films. The thickness of the backing layer is suitably determined to prevent patient discomfort upon adhesion to the skin. The backing layer preferably has a thickness from 10 µm to 200 µm, more preferably from 10 µm to 50 µm.

In the present invention, the peripheral adhesive backing layer is a film or textile to which an adhesive is applied, and improves adhesion of patches when attached to the skin together with a patch while adhering to the backing layer opposite to the drug-adhesive layer of the patch. The peripheral adhesive backing layer usable in the present invention means a film to which an adhesive material is applied. As the film, any moisture permeable and breathable substances may be used. Examples of the film may include films having flexibility such as polyurethane films, ethylene vinyl acetate copolymer films, polyethylene films etc., porous films, perforated films, various natural and synthetic textiles obtained through weaving and spinning, processed articles in non-woven fabric shape and thin foams formed by incorporating a foaming agent into a polymer etc. A breathable backing layer such as polyurethane films, porous films, perforated films, various natural and synthetic textiles obtained through weaving and spinning, processed articles in non-woven fabric shape and thin foams formed by incorporating a foaming agent into a polymer etc. is preferred. Polyurethane films and porous films are more preferred.

The adhesive material used in the peripheral adhesive backing layer refers to various materials ranging from acrylic type adhesives to rubber type, silicone type, and EVA type adhesives.

The detachable film according to the present invention serves to provide convenience so that the drug-containing adhesive layer is protected during storage of products and is easily detachable when the product is used. Examples of the detachable film may include films made from polyesters, polyvinyl chloride, polyvinylidene chloride, polyethylene terephthalate etc., or laminated films of wood-free paper or glassine paper as paper with polyolefin, without being specifically limited thereto. The detachable film refers to a film in which a surface in contact with the drug-adhesive layer is coated with a silicone resin, a lipid resin or a fluorine resin. A polyethylene terephthalate film ensuring long term drug stability is preferably used as the detachable film.

A fentanyl transdermal patch according to the present invention may be prepared by a simple preparation method, maintain constant fentanyl skin permeability for three days while maintaining close contact with the skin, prevent detachment due to moisture and sweat, and suppress skin irritation.

DETAILED DESCRIPTION

Figure 1:
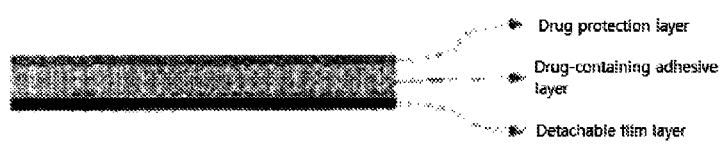
FIG. 1 is a sectional view of one embodiment of a fentanyl transdermal patch according to the present invention.
Figure 2:
FIG. 2 is a sectional view of another embodiment of a fentanyl transdermal patch according to the present invention.

Hereinafter, the constitution and functions of the present invention will be explained in more detail with reference to the following examples. It should be understood that these examples are provided for illustration only and are not to be in any way construed as limiting the present invention. Further, the order in which each component is added during the preparation process is for illustrative purposes only and the present invention is not limited thereto.

EXAMPLES

Example 1

In a 250 mL glass container, 100 g (solid content of 49 g) of an acrylic-rubber hybrid adhesive (Duro-Tak 87-504A, made by Henkel Corporation), 30 g of toluene, and 33.5 g of ethyl acetate were uniformly mixed using a roll mixer such that the acrylic-rubber hybrid adhesive was diluted to a solid content of 30%. A 30 mL glass vial was charged with 18 g (solid content of 5.4g) of the diluted Duro-Tak 87-504A adhesive and 0.6 g of fentanyl, thereby completely dissolving fentanyl in the adhesive solution. The adhesive solution containing dissolved fentanyl was coated onto a silicone-coated 75 μm thick polyethylene terephthalate (PET) film to have a post-drying thickness of 40 μm, and then dried. One side of the resulting film was covered and laminated with a PET side of a film, which was formed by stacking a 40 μm thick polyethylene (PE) film on a 12 μm thick PET film, followed by cutting to a size of 21 cm$^2$ to prepare patches.

Example 2

In a 250 mL glass container, 100 g (solid content of 43.5 g) of Duro-Tak 87-503A (Henkel Corporation) as an acrylic-rubber hybrid adhesive instead of Duro-Tak 87-504A, 20 g of toluene, and 25 g of ethyl acetate were mixed using a roll mixer such that the acrylic-rubber hybrid adhesive was diluted to a solid content of 30%. Patches were prepared in the same manner as in Example 1 using the diluted Duro-Tak 87-503A adhesive.

Example 3

A 30 mL glass vial was charged with 16 g (solid content of 4.8 g) of the diluted Duro-Tak 87-504A adhesive and 1.2 g of fentanyl, thereby completely dissolving fentanyl in the adhesive solution. The adhesive solution containing dissolved fentanyl was coated onto a silicone-coated 75 μm thick polyethylene terephthalate (PET) film to have a post-drying thickness of 20 μm, and then dried. One side of the resulting film was covered and laminated with a PET side of a film, which was formed by stacking a 40 μm thick polyethylene (PE) film on a 12 μm thick PET film, followed by cutting to a size of 21 cm$^2$ to prepare patches.

Example 4

A 30 mL glass vial was charged with 16 g (solid content of 4.8 g) of the diluted Duro-Tak 87-504A adhesive, 0.6 g of fentanyl, and 0.6 g of glycerol monooleate (GMO, PECEOL® Gatte Fosse), thereby completely dissolving fentanyl and GMO in the adhesive solution. Patches were prepared in the same manner as in Example 1.

Example 5

Duro-Tak 87-202A (Henkel Corporation), as an adhesive, was coated onto a silicone-coated 75 μm thick polyethylene terephthalate film and then dried to a thickness of 30 μm. The dried adhesive layer was covered and laminated with a polyurethane side of the polyurethane film (Jeungwoo PU Co., Ltd., polyurethane thickness 20 μm) using, as a carrier, a release paper in which polyethylene was laminated onto paper and which was subjected to silicone treatment. The PET release film was detached and the PE side of the PET/PE laminated film of the patch prepared as in Example 1 was attached to the adhesive layer coated onto the polyurethane, and then a PET release film was detached from the patch. This was covered with a 50 μm thick PET release film which was subjected to silicone treatment such that the film was placed in the middle of the patch, followed by cutting to a size of 35 cm$^2$ to prepare patches.

Example 6

Patches were prepared in the same manner as in Example 3 using propylene glycol monolaurate (Lauroglycol® 90, Gatte Fosse) instead of glycerol monooleate.

Example 7

Patches were prepared in the same manner as in Example 3 using sorbitan monooleate (Span 80, made by Japan Junyaku Co., Ltd.) instead of glycerol monooleate.

Example 8

Patches were prepared in the same manner as in Example 3 using lauryl pyrrolidone (Surfadone® LP-300, ISP) instead of glycerol monooleate.

Example 9

A 30 mL glass vial was charged with 0.1 g of polyvinyl pyrrolidone (PVP) K-25 (Plasdone® K-25, BASF) and 2 g of isopropanol, thereby completely dissolving PVP K-25 in isopropanol. When PVP K-25 was completely dissolved, 15.65 g (solid content of 4.7 g) of the diluted Duro-Tak 87-504A adhesive, 0.6 g of fentanyl and 0.6 g of glycerol monooleate (GMO, PECEOL® Gatte Fosse) were charged to a 30 mL glass vial, thereby completely dissolving fentanyl and GMO in the adhesive solution. Thereafter, patches were prepared in the same manner as in Example 1.

Comparative Example 1

In a 250 mL glass container, 100 g (solid content of 39 g) of an acrylic adhesive (Duro-Tak 87-4287, made by Henkel Corporation) and 30 g of toluene were mixed using a roll mixer such that the acrylic adhesive was diluted to a solid content of 30%. A 30 mL glass vial was charged with 18 g (solid content of 5.4 g) of the diluted Duro-Tak 87-4287 adhesive and 0.6 g of fentanyl, thereby completely dissolving fentanyl in the adhesive solution. Thereafter, patches were prepared in the same manner as in Example 1.

Comparative Example 2

In a 250 mL glass container, 100 g (solid content of 33.5 g) of an acrylic adhesive (Duro-Tak 87-2852, made by Henkel Corporation) and 11.65 g of toluene were mixed using a roll mixer such that the acrylic adhesive was diluted to a solid content of 30%. A 30 mL glass vial was charged with 18.0 g (solid content of 5.4g) of the diluted Duro-Tak 87-2852 adhesive and 0.6 g of fentanyl, thereby completely dissolving fentanyl in the adhesive solution. Thereafter, patches were prepared in the same manner as in Example 1.

Comparative Example 3

In a 250 mL glass container, 100 g (solid content of 38.5 g) of an acrylic adhesive (Duro-Tak 87-4098, made by Henkel Corporation) and 28.35 g of toluene were mixed using a roll mixer such that the acrylic adhesive was diluted to a solid content of 30%. A 30 mL glass vial was charged with 18.0 g (solid content of 5.4g) of the diluted Duro-Tak 87-4287 adhesive and 0.6 g of fentanyl, thereby completely dissolving fentanyl in the adhesive solution. Thereafter, patches were prepared in the same manner as in Example 1.

Comparative Example 4

A 30 mL glass vial was charged with 10 g of a solution (solid content of 1 g) in which a high molecular weight polyisobutylene rubber (Oppanol B-100, made by BASF) was dissolved in toluene in a concentration of 10%, 5 g of a solution (solid content of 2 g) in which a low molecular weight polyisobutylene rubber (HIMOL 5H, made by NIPPON PETROCHEMICALS CO. LTD.) was dissolved in a concentration of 40%, 2.1 g of terpene resin (Sylvares TR7115, made by Arizona chemical), and 0.6 g of mineral oil (Kaydol, made by Sonneborn, INC.), thereby completely dissolving fentanyl in the adhesive solution. The adhesive solution containing dissolved fentanyl was coated onto a silicone-coated 75 μm polyethylene terephthalate (PET) film and then dried to a thickness of 80 μm. One side of the resulting film was covered and laminated with a PET side of a film, which was formed by stacking a 40 μm thick polyethylene (PE) film on a 12 μm thick PET film, followed by cutting to a size of 21 cm$^2$ to prepare patches.

Experimental Examples

In order to evaluate the quality of the patches prepared in Examples, transdermal permeation testing, adhesion testing and attachment testing were performed. As Reference Example, the same tests were performed on a commercially available fentanyl patch, Durogesic D-trans (3 day-formulation, made by Janssen Korea Co., Ltd.).

Skin Permeation Testing

Skin permeation testing was performed on the patches prepared in Examples 1~9 and Comparative Examples 1~4 and Durogesic D-trans patches (Reference Example).

Specifically, the skin permeation testing was performed under sink conditions using a Franz diffusion cell (effective area: 0.64 cm$^2$, volume of receptor fluid: 5.2 ml). As the receptor fluid, phosphate buffered saline (PBS) having a pH of 7.4 was used. First, a Franz diffusion cell was charged with the receptor fluid and then maintained at 32±0.5° C. The sample was cut into a circular shape (area of 0.64 cm$^2$) and then attached to the center of human cadaver epidermis. The skin onto which sample was attached was put on the top of the receptor chamber of the Franz diffusion cell. After covering the donor portion and fixing using a clamp, experimentation was performed by rotating a magnetic bar at a rate of 600 rpm. At the time of 3, 6, 9, 12, 24, 36, 48, 60, and 72 hours, 250 μl of receptor fluid was taken from each cell and then the same amount of fresh receptor fluid was added. The content of fentanyl in the collected receptor fluid layer was analyzed by HPLC. Conditions for HPLC analysis were suitably adapted by adjusting the flow rate and the injected amount based on the analysis conditions of fentanyl citrate as prescribed in USP 29. Experiment results are shown in Table 1 and FIGS. 3 and 4.

TABLE 1

| | $J_{max}$[a] (μg/cm$^2$/h) | $J_{0-24}$[b] (μg/cm$^2$/h) | $J_{24-72}$[c] (μg/cm$^2$/h) | $J_{0-24}/J_{24-72}$[d] |
|---|---|---|---|---|
| Reference Example | 4.91 | 3.40 | 1.82 | 53.6% |
| Example 1 | 5.67 | 3.92 | 2.46 | 62.8% |
| Example 2 | 5.33 | 3.83 | 2.35 | 61.4% |
| Example 3 | 6.33 | 5.27 | 3.10 | 58.8% |
| Example 4 | 6.63 | 4.88 | 2.73 | 56.0% |
| Example 6 | 5.83 | 4.78 | 2.64 | 55.1% |
| Example 7 | 5.92 | 4.38 | 2.62 | 59.8% |
| Example 8 | 6.60 | 5.27 | 2.81 | 53.3% |
| Example 9 | 5.72 | 4.60 | 2.78 | 60.5% |
| Comparative Example 1 | 4.65 | 3.21 | 2.02 | 62.8% |

TABLE 1-continued

|  | $J_{max}$[a] ($\mu$g/cm$^2$/h) | $J_{0\text{-}24}$[b] ($\mu$g/cm$^2$/h) | $J_{24\text{-}72}$[c] ($\mu$g/cm$^2$/h) | $J_{0\text{-}24}/J_{24\text{-}72}$[d] |
|---|---|---|---|---|
| Comparative Example 2 | 2.95 | 2.04 | 1.09 | 53.6% |
| Comparative Example 3 | 3.85 | 2.83 | 1.58 | 56.0% |
| Comparative Example 4 | 5.06 | 3.50 | 1.88 | 53.6% |

[a] $J_{max}$: Maximum skin permeation rate during the experiment
[b] $J_{0\text{-}24}$: Average skin permeation rate during 0-24 hours of the experiment
[c] $J_{24\text{-}72}$: Average skin permeation rate during 24-72 hours of the experiment
[d] $J_{0\text{-}24}/J_{24\text{-}72}$: Ratio of average skin permeation rate during 0-24 hours to average skin permeation rate during 24-72 hours of the experiment As the results of skin permeation experiments, the maximum skin permeation rate ($J_{max}$), average skin permeation rate ($J_{0\text{-}24}$) from initiation to 24 hours, and average skin permeation rate ($J_{24\text{-}72}$) from 24 hours to 72 hours are as shown in Table 1. In the ratio of average skin permeation rate during 0-24 hours versus average skin permeation rate during 24-72 hours of the experiment ($J_{0\text{-}24}/J_{24\text{-}72}$), all the Examples showed higher values than the Reference Example, from which it was found that patches of Examples could deliver drugs at a consistent rate for 72 hours as compared to the patch of the Reference Example.

Figure 3:
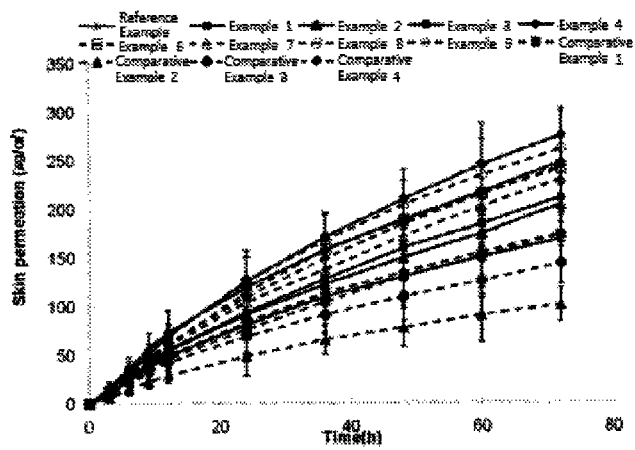
FIG. 3 shows accumulated skin permeation of fentanyl of patches prepared in Examples, Comparative Examples, and Reference Example.
Figure 4:
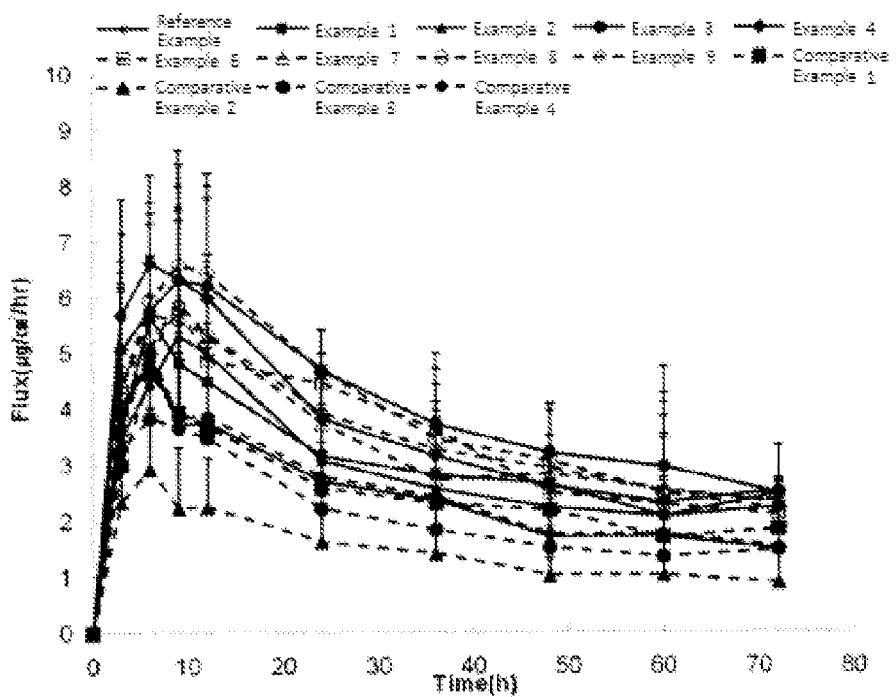
FIG. 4 shows skin permeation rates of the patches prepared in Examples, Comparative Examples, and Reference Example.

As shown in FIGS. 3 and 4, the patches of the Examples can initially deliver drugs at a high rate and, after arriving at maximum skin permeation rate, the skin permeation rate of the patches of Examples gradually decreased. After 24 hours, the decrease degree was diminished, and drugs permeated the skin at a near constant rate. Further, it could be seen that the patches of Examples showed higher permeation rate than the patches of Reference Example and Comparative Examples. From the results, it could be seen that the patches of Examples can rapidly deliver more amounts of the drug through skin than other patches having the same area.

Adhesion Testing

Adhesion was measured using a tensile strength tester. Testing was performed by testing three times in accordance with a probe tack test (ASTM D2979), thereby calculating an average value. Results are shown in Table 2.

TABLE 2

|  | Ex 1 | Ex 2 | Ex 3 | Ex 4 | Ex 5 | Ex 6 | Ex 7 | Ex 8 | Ex 9 | Reference Example |
|---|---|---|---|---|---|---|---|---|---|---|
| Probe tack (gf) | 1291 | 1225 | 1258 | 1389 | 1289 | 1374 | 1401 | 1302 | 1395 | 1319 |

As confirmed in Table 2, the adhesion of the patches according to the present invention was equal or much better than that of the patch of Reference Example.

Attachment Testing

Since fentanyl is a narcotic agent, top six patches in Probe tack experiments of Examples 1~9 and a patch of Reference Example were attached to dorsal portions of 10 hairless mice for 72 hours. Attachment testing was performed as shown in Table 3 and average values are shown in Table 4. For reference, results of attachment testing performed on mice were assumed to correspond to about 70% for the values obtained when attached to humans, when considering the activity of mice.

TABLE 3

|  | Maintain attachment for 3 days | Maintain attachment for 2 days | Maintain attachment for 1 day |
|---|---|---|---|
| Point | 3.0 | 2.0 | 1.0 |

TABLE 4

|  | Ex. 1 | Ex. 4 | Ex. 5 | Ex. 6 | Ex. 7 | Ex. 9 | Reference Example |
|---|---|---|---|---|---|---|---|
| Average value | 2.3 | 2.4 | 3 | 2.6 | 2.4 | 2.8 | 3.4 |

As shown in Table 4, top six patches in Probe tack experiments of Examples 1~9 according to the present invention exhibited the same or much better attachment than the patch of Reference Example for 3 day-formulation. Specifically, the patch of Example 5 including the peripheral adhesive backing layer was attached for 3 days though the mouse was very active.

What is claimed is:

1. A fentanyl transdermal patch comprising:
a backing layer and a drug-adhesive layer at one side of the backing layer, wherein the drug-adhesive layer comprises 90 parts by weight to 60 parts by weight of an acrylic-rubber hybrid polymer, and 5 parts by weight to 20 parts by weight of at least one drug selected from fentanyl, fentanyl derivatives and pharmaceutical salts thereof, based on 100 parts by weight of the drug adhesive layer.

2. The fentanyl transdermal patch according to claim 1, wherein the fentanyl derivative is alfentanyl, carfentanyl, lofentanyl, remifentanyl, sufentanil, or trefentanyl.

3. The fentanyl transdermal patch according to claim 1, wherein the drug-adhesive layer has a thickness ranging from 20 $\mu$m to 200 $\mu$m.

4. The fentanyl transdermal patch according to claim 1, wherein the acrylic-rubber hybrid polymer is formed by grafting a rubber polymer of polyethylene-butylene, polyethylene-vinyl acetate, polybutylene, polystyrene-isoprene, or polystyrene-isoprene-butadiene to an acrylic polymer selected from the group consisting of 2-ethylhexyl acrylate, butyl acrylate, isooctyl acrylate, methyl acrylate, methyl methacrylate, acrylic acid, 2-hydroxyethyl acrylate, and vinyl acetate.

5. The fentanyl transdermal patch according to claim 1, further comprising: 5 parts by weight to 20 parts by weight of at least one transdermal absorption enhancer selected from the group consisting of N-methyl-2-pyrrolidone, N-caprylic-2-pyrrolidone, N-dodecyl-2-pyrrolidone, glycerol lauryl alcohol, oleyl alcohol, isopropyl myristate, sorbitan monooleate, propylene monolaurate, propylene monooleate, oleyl macrogoglyceride, oleic acid, lauroyl macrogoglyceride, linoleoyl macrogoglyceride, propyleneglycol caprylate/caprate, sorbitan monostearate monooleate, glycerol monolaurate, propylene glycol monolaurate, propyleneglycol monocaprylate, sorbitan monolaurate, lauryl lactate, caprylic/capric triglyceride, corn oil PEG-8 ester, corn oil PEG-6 ester, and triacetin, based on the total amount of the drug-adhesive layer.

6. The fentanyl transdermal patch according to claim 1, further comprising: 5 parts by weight to 20 parts by weight of at least one tackifier selected from the group consisting of glycerin rosin ester, hydrogenated glycerin rosin ester, terpene resins, aliphatic hydrocarbon, cycloaliphatic hydrocarbon, DCPD (dicyclo pentadiene), coumarone-indene, polypyrrolidone, polyacrylate, hydroxypropylcellulose, and polybutene resins, based on the total amount of the drug-adhesive layer.

7. The fentanyl transdermal patch according to claim 1, further comprising: a detachable film layer on one side of the drug-adhesive layer.

8. The fentanyl transdermal patch according to claim 1, further comprising: a peripheral adhesive backing layer on one side of the backing layer.

9. The fentanyl transdermal patch according to claim 1, wherein the backing layer is a polyester film, a multi-deposited film, an aluminum-deposited polyester film, or a non-woven fabric-laminated polyester film.

10. The fentanyl transdermal patch according to claim 8, wherein the peripheral adhesive backing layer is obtained by coating an acrylic, rubber, silicone, or EVA adhesive onto a polyurethane film, an ethylene vinyl acetate copolymer film, a polyethylene film, a porous film, a perforated film, natural and synthetic fabrics obtained through weaving and spinning, processed articles in non-woven fabric form, or thin foams formed by incorporating a foaming agent into a polymer.

11. The fentanyl transdermal patch according to claim 7 wherein the detachable film layer is a polyester film, a polyvinyl chloride film, a polyvinylidene chloride film, a polyethylene terephthalate film, wood free paper, glassine paper, or a film in which a silicone resin or fluorine resin is coated onto a polyolefin film.

* * * * *